United States Patent [19]

Lassen et al.

[11] 4,275,209
[45] Jun. 23, 1981

[54] XANTHENE AND THIOXANTHENE DERIVATIVES

[75] Inventors: Niels Lassen, Gentofte; Klaus P. Bøgesø, Lyngby; Peter B. Hansen, Allerød; Jørn L. M. Buus, Bjæverskov; Allan J. Bigler, Copenhagen, all of Denmark

[73] Assignee: Kefalas A/S, Copenhagen-Valby, Denmark

[21] Appl. No.: 106,353

[22] Filed: Dec. 21, 1979

Related U.S. Application Data

[62] Division of Ser. No. 35,735, May 3, 1979.

[30] Foreign Application Priority Data

May 12, 1978 [GB] United Kingdom ............... 19310/78

[51] Int. Cl.$^3$ ........................................... C07D 409/04
[52] U.S. Cl. .................................. 546/202; 260/335; 424/248.51; 424/250; 424/251; 424/267; 544/63; 544/96; 544/130; 544/238; 544/316; 544/319; 544/333; 544/364; 546/187; 546/196; 549/27
[58] Field of Search ............... 546/196, 202, 203, 187; 544/63, 96, 130, 238, 316, 319, 333, 364

[56] References Cited

U.S. PATENT DOCUMENTS

| | | | |
|---|---|---|---|
| 3,470,188 | 9/1969 | Kaiser et al. | 546/196 X |
| 4,031,222 | 6/1977 | Remy | 546/203 X |
| 4,073,912 | 2/1978 | Kaiser et al. | 546/202 X |
| 4,086,350 | 4/1978 | Zirkle | 546/202 X |

*Primary Examiner*—Richard A. Schwartz
*Attorney, Agent, or Firm*—Gordon W. Hueschen

[57] ABSTRACT

The present invention relates to novel thioxanthene and xanthene derivatives which have useful pharmacodynamic activity, such as neuroleptic activity and antiemetic activity, methods for the preparation of said derivatives, pharmaceutical compositions containing same, and a method for the treatment of psychic disorders by administering a therapeutically active amount of one of said derivatives to a living animal body, including human beings.

The new compounds of the present invention corresponds to the Formula I:

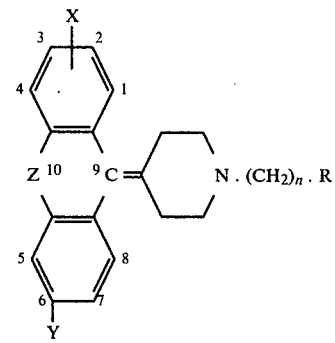

wherein X is a halogen atom, an alkyl group with from one to four carbon atoms inclusive, an alkyloxy group with from one to four carbon atoms inclusive, a methylthio group, a methylsulphonyl group, a dimethylsulfamoyl group, a trifluoromethyl group or an acetyl group;

Y is hydrogen, fluorine or a methyl group;

Z is oxygen or sulphur;

n is an integer from zero to three inclusive, and

R is a cycloalkyl group with from four to six carbon atoms inclusive in the ring substituted with from one to four substituents selected from optionally esterified hydroxy- or hydroxymethyl groups, methyl groups, amino groups, acetamido groups, mesylamino groups or oxo groups, a five- or six-membered saturated heterocyclic ring having one or two heteroatoms selected from oxygen and nitrogen atoms and being optionally substituted with an optionally esterified hydroxy group or oxo group, any esterified hydroxy group present being an ester of an aliphatic carboxylic acid having from ten to twentytwo carbon atoms inclusive, as well as their non-toxic pharmaceutically acceptable acid addition salts.

3 Claims, No Drawings

XANTHENE AND THIOXANTHENE DERIVATIVES

This is a division of application Ser. No. 035,735, filed May 3, 1979.

BACKGROUND OF THE INVENTION

In the past, several drugs having a tricyclic structure have been found useful in the treatment of severe psychotic disorders, especially of the schizophrenic type. Some of these drugs are thioxanthenes which are substituted in the 2-position of one of the benzene rings, and some of the most active are described in U.S. Pat. No. 3,116,291. Recently some thioxanthenes having a fluoro atom in the 6-position have been described, for example in U.S. Pat. No. 4,042,695 as having neuroleptic properties of the same level as the known thioxanthene-neuroleptics but a much lower level of pharmacological effects associated with extrapyrimidal symptoms. Further, some piperidylidene-thioxanthene derivatives having almost no extrapyrimidal side effects have been described in Belgian Pat. No. 835,224. However, the said known thioxanthene compounds which have the lowest extrapyrimidal side effects also have relatively short-acting neuroleptic effects.

SUMMARY OF THE INVENTION

According to the present invention it has now surprisingly been found that the compounds of Formula I as well as their non-toxic acid addition salts have both strong and very long-lasting neuroleptic effects and, at the same time, a pharmacological profile which indicates relatively low extrapyrimidal side effects when they are evaluated according to standard reliable published test methods. They also have a low acute toxicity compared with related thioxanthene derivatives, which makes the therapeutic index favorable. Moreover, they have moderately strong anticholinergic effects, and comparatively low undesired sedative effect.

This invention also includes pharmaceutically acceptable salts of the compounds of Formula I formed with non-toxic organic acids. Such salts are easily prepared by methods known to the art. The base is reacted with either the calculated amount of organic or inorganic acid in an aqueous miscible solvent, such as acetone or ethanol, with isolation of the salt by concentration and cooling or an excess of the acid in aqueous immiscible solvent, such as ethyl ether or chloroform, with the desired salt separating directly. Exemplary of such organic salts are those with maleic, fumaric, benzoic, ascorbic, embonic, succinic, oxalic, bis methylene-salicylic, methanesulfonic, ethanedisulfonic, acetic, propionic, tartaric, salicylic, citric, gluconic, lactic, malic, mandelic, cinnamic, citraconic, aspartic, stearic, palmitic, itaconic, glycolic, p-amino-benzoic, glutamic, benzene sulfonic and theophylline acetic acids as well as the 8-halotheophyllines, for example 8-bromotheophylline. Exemplary of such inorganic salts are those with hydrochloric, hydrobromic, sulfuric, sulfamic, phosphoric and nitric acids. Of course, these salts may also be prepared by the classical method of double decomposition of appropriate salts, which is wellknown to the art.

The compounds of Formula I may exist in form of isomers of the cis-trans type, and the present invention comprises the single isomers as well as mixtures of the isomers. The novel xanthene and thioxanthene derivatives of the invention may be administered both orally and parenterally, for example in the form of tablets, capsules, powders, syrups, suppositories or solutions or suspensions for injection.

The invention moreover relates to a method for the preparation of the novel compounds of Formula I, which comprises (a) reacting a compound of the following formula:

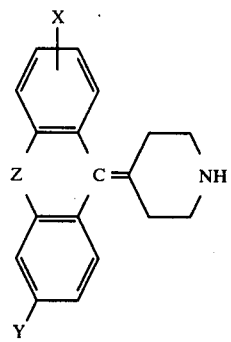

II wherein X, Y and Z are as defined above with a reactive ester of a compound of the formula $HO.(CH_2)_n.R$ 

wherein n and R are as above defined and any hydroxy or amino group present is protected by esterification, or (b) reducing a compound of the formula:

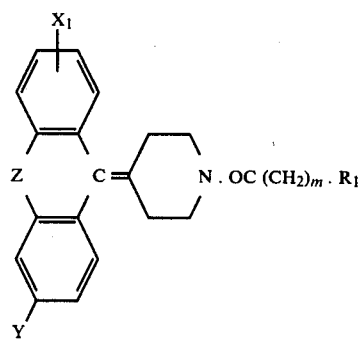

III wherein Y and Z are as defined above, $R_1$ is as R except that it has no oxo-group and any hydroxy group is protected, $X_1$ is a halogen atom, an alkyl group with from one to four carbon atoms inclusive, an alkyloxy group with from one to four carbon atoms inclusive, a methylmercapto group or a trifluoromethyl group; and "m" is an integer from zero to two, with lithium aluminium hydride, or (c) reducing a compound of the formula:

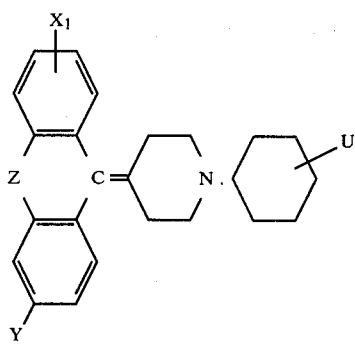

wherein $X_1$, Z and Y are as defined above, and U is —COOH or —OOC.phenyl with lithium aluminium hydride in order to obtain a compound of the formula:

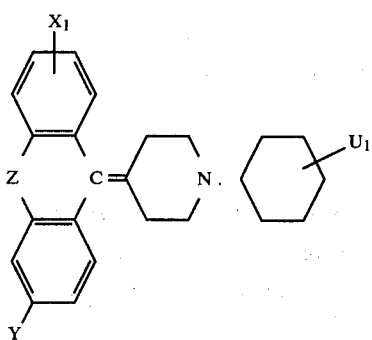

wherein $X_1$, Z and Y are as defined above and $U_1$ is —CH$_2$OH or —OH respectively, or (d) reducing a compound of the formula:

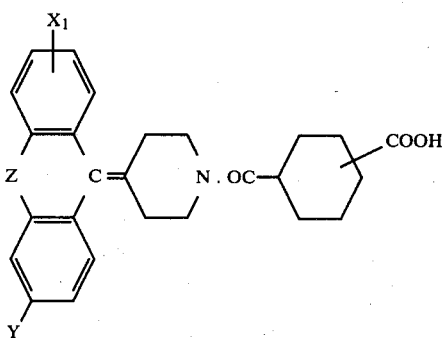

wherein $X_1$ and Y are as defined above with lithium aluminium hydride in order to obtain a compound of the formula:

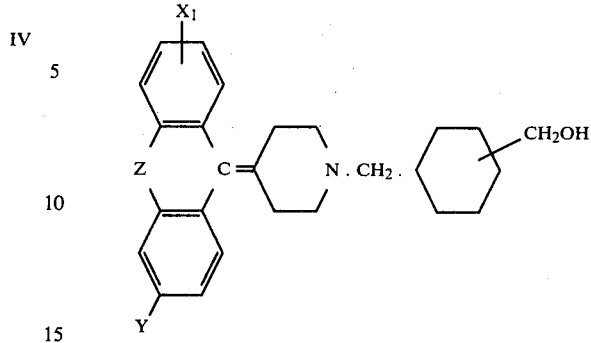

or (g) oxidizing a compound of the formula:

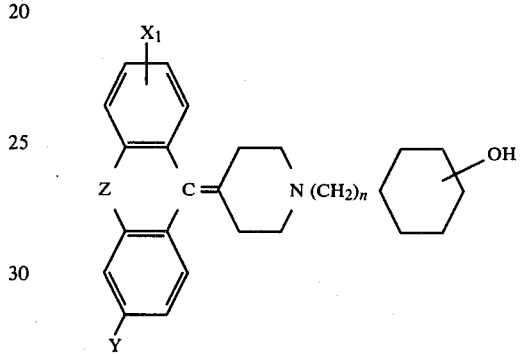

wherein $X_1$, Z, Y and n are as defined above, by means of a ketone in the presence of an aluminum alkoxide, in order to obtain a compound of Formula I, wherein R is a cyclohexanone group, whereupon the compound of Formula I obtained is isolated, and any hydroxy group present optionally esterified with a reactive derivative of an aliphatic carboxylic acid having from ten to twenty-two carbon atoms inclusive and, if desired, acetylating or mesylating any amino group present in well-known manner, as the free base or a non-toxic acid addition salt thereof.

Several of the intermediates of Formula II and all the intermediates of Formula III–VII are novel compounds and fall within the scope of the present invention.

The intermediates of Formula II may conveniently be prepared according to the following reaction scheme:

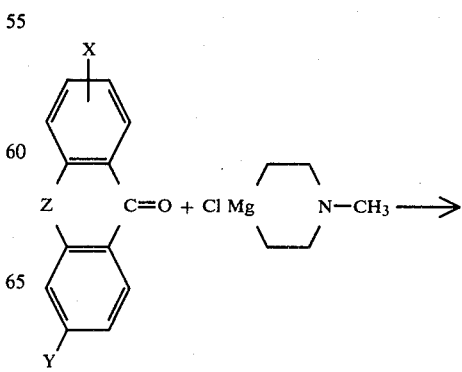

-continued

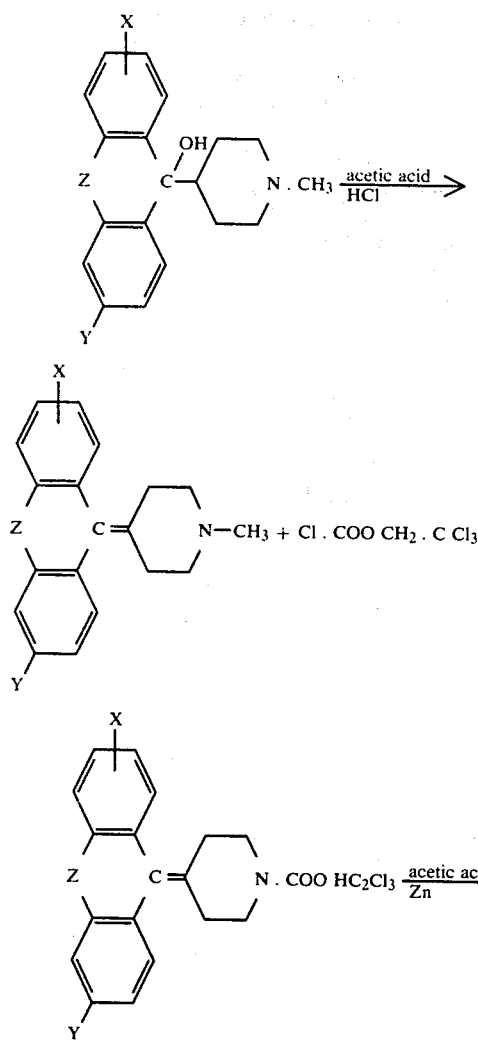

except that X may not be an acetyl group.

When preparing compounds of Formula II wherein X is acetyl they may conveniently be prepared as described in Belgian Pat. No. 558,171 according to the following scheme

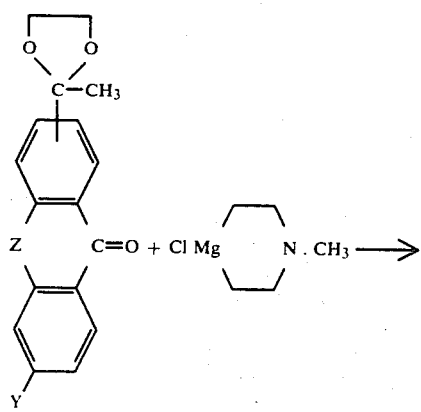

-continued

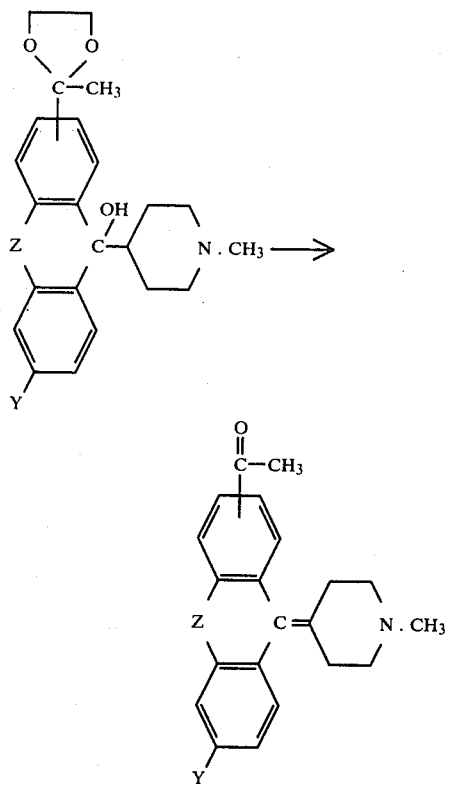

the further processing being as described above.

The intermediates of Formula III may conveniently be prepared in the following way:

any protecting group being removed before reduction with lithium aluminum hydride.

Any other obvious chemically equivalent method for the preparation of the amides of Formula III may of course be used.

The intermediates of Formula III may also be prepared in the following way:

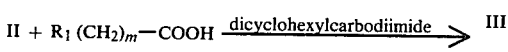

The intermediates of Formula IV may according to the invention be prepared by a reductive alkylation of compounds of Formula II with compounds of the formula:

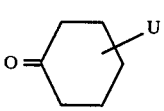

wherein U is as defined above by means of sodium cyanoboron hydride (NaCNBH$_3$).

The intermediates of Formula V, where —COOH is in ortoposition, may according to the invention be prepared by reacting a compound of Formula II with 1,2-cyclohexanedicaboxylic acid anhydride.

Some of the xanthones and thioxanthones used as starting materials for the preparation of the intermediates of Formula II are known substances, the preparation of which is described for example in U.S. Pat. Nos. 3,116,291 and 4,042,695 and Belgian Pat. No. 558,171. Others are new but they are prepared by methods known in the art for the preparation of similar substances.

In method (a) the reactive esters of the compounds of formula HO.(CH$_2$)$_n$.R may according to the invention conveniently be esters of hydrogen halide, such as hydrogen chloride or hydrogen bromide, or esters of organic sulphonic acids, such as methane sulphonic acid, ethane sulphonic acid, p-toluene sulphonic acid or the like. Otherwise, the reaction (a) is a wellknown reaction type, which is normally carried out in inert organic solvents and under basic conditions in order to neutralize the acid formed by the reaction.

The reductions according to methods (b), (c) or (e) may according to the invention conveniently be carried out by lithium aluminium hydride or similar reducing agents which will not at the same time reduce the double bond between the thiaxanthene and piperidine rings.

The oxidation according to method (g) of the invention is a socalled Oppenauer Oxidation and may according to the invention be carried out in the presence of an excess of a ketone (preferably cyclohexanone or acetone), in the presence of an aluminium alkoxide (preferably aluminiumisopropoxide).

The optional esterification of any hydroxy group or groups present in the compound of Formula I may according to the invention conveniently be carried out by a reactive derivative of the carboxylic acid having from ten to twenty-two carbon atoms inclusive, such as an acid chloride or anhydride. As carboxylic acids may be mentioned decanoic acid, palmitic acid and behenic acid.

The optional acetylation or mesylation of any amono group present in a compound of Formula I may be carried out in conventional manner by treatment with acetic anhydride, acetylchloride or mesylchloride.

The methods of the invention shall in the following be illustrated by some examples which may not be construed as limiting:

EXAMPLE 1

Preparation of the starting compounds of Formula II: 4-(2-trifluoromethyl-6-fluoro-9-hydroxy-9-thioxanthenyl)-1-methyl piperidine.

In a 3 liter three necked flask equipped with stirrer, reflux condenser and separatory funnel were placed 60 grams of magnesium filings, 1.5 liter of dry tetrahydrofuran and a few crystals of iodine, whereupon 1 milliliter of ethylene bromide was added and the mixture warmed until the reaction starts. After the reaction has been completed 300 grams of freshly distilled 4-chloro-1-methylpiperidine were added while stirring at a rate which makes the reaction mixture boil by the heat of reaction. After the addition has been completed the reaction mixture was heated under reflux for three hours. Thereafter the reaction mixture was cooled in an ice bath and 430 grams of 2-trifluoro-acetyl -6-fluoro-9-thioxanthone (preparation described in U.S. Pat. No. 4,042,695) were added portion-wise while stirring and keeping the temperature at 10–20 degrees Centigrade. Thereafter the reaction mixture was stirred without cooling for 30 minutes. The dark coloured reaction mixture was poured onto crushed ice, acetic acid was added until the magnesium hydroxide precipitated had been dissolved, and the aqueous phase washed with 4 liters of ether. The organic phase was extracted twice with 1 liter of 10% acetic acid. The combined aqueous phase was made basic with aqueous ammonia and the base which separated out was extracted with ether. The ether extract was dried over anhydrous potassiumcarbonate, treated with active carbon and evaporated to a volume of about one liter. By cooling and standing 385 grams of 4-(2-trifluoromethyl-6-fluoro-9-hydroxy-9-thioxanthenyl)-1-methyl-piperidine were obtained as white crystals which melted at 250–255 degrees Centigrade.

In corresponding manner the xanthenols and thioxanthenols of this formula were prepared:

| X | Y | Z | MP in degrees Centigrade |
|---|---|---|---|
| 2-CF$_3$ | H | S | 240–242 |
| 2-Cl | H | S | 200–205 |
| 2-Cl | F | S | 225–230 |
| 2-SCH$_3$ | H | S | 190–195 |
| 2-SCH$_3$ | F | S | 180–189 |
| 3-F | H | S | 195–198 |
| 3-F | F | S | 210–211 |
| 2-CH$_3$ | F | S | 200–220 |
| 2-F | CH$_3$ | S | 178–180 |
| 2-SO$_2$N(CH$_3$)$_2$ | F | S | 210–220 |
| 2-SO$_2$CH$_3$ | H | S | 252–260 |
| 2-OCH$_3$ | F | S | 183–185 |
| 2-CF$_3$ | CH$_3$ | S | 235–238 |
| 2-C(O)OCH$_3$ (cyclic) | H | S | 206–208 |
| 2-OCH$_3$ | H | S | 175–177 |
| 2-SCH$_3$ | F | O | 164–166 |
| 2-Cl | H | O | 205–210 |

4-(2-trifluoromethyl-6-fluoro-9-thioxanthenylidene)-1-methyl-piperidine.

100 grams of 4-(2-trifluoromethyl-6-fluoro-9-hydroxy-9-thioxanthenyl)-1-methyl piperidine were disssolved in a mixture of 500 milliliters of glacial acetic acid and 300 milliliters of concentrated hydrochloric acid. The reaction mixture was heated under reflux for 2½ hour, whereupon the major part of the acid mixture was distilled off and the residue poured into ice water. The aqueous solution was made basic with aqueous ammonia and extracted with ether. The ether phase was dried over anhydrous potassium carbonate, treated with active carbon and evaporated to about 300 milliliters. Upon cooling and standing 76 grams of 4-(2-trifluoromethyl-6-fluoro-9-thioxanthenylidene)-1-methyl-piperidine were obtained as white crystals which melted at 100–102 degrees Centigrade.

In corresponding manner were prepared the compounds of the following formula:

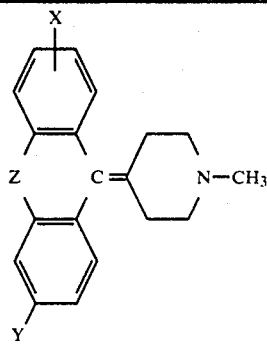

| X | Y | Z | MP in degrees Centigrade |
|---|---|---|---|
| 2-CF₃ | H | S | 100-102 |
| 2-Cl | H | S | Oil |
| 2-Cl | F | S | 130-132 |
| 2-SCH₃ | H | S | 104-106 |
| 2-SCH₃ | F | S | 114-117 |
| 3-F | H | S | 115-117 |
| 3-F | F | S | 138-140 |
| 2-CH₃ | F | S | 90-92 |
| 2-F | CH₃ | S | 93-96 |
| 2-SO₂N(CH₃)₂ | F | S | 160-162 |
| 2-SO₂CH₃ | H | S | 162-166 |
| 2-OCH₃ | F | S | 125-127 |
| 2-CF₃ | CH₃ | S | 157-160 |
| 2-COCH₃ | H | S | 125-127 |
| 2-OCH₃ | H | S | 102-104 |
| 2-SCH₃ | F | O | 134-136 |
| 2-Cl | H | O | Oil |

The compound 4-(2-acetyl-9-thioxanthenylidene)-1-methylpiperidine, was prepared in the following way:

140 grams of the ethylene glycal ketal of 2-acetyl-9-(1-methyl-4-piperidyl)-9-thioxanthenol (MP 206-208 degrees Centigrade) were heated for two hours under reflux with a mixture of 1500 milliliters of propionic acid and 100 grams of 2-sulfobenzoic acid anhydride. Thereafter the mixture was evaporated in vacuum, the residue dissolved in water and made alkaline. The base which separated out was extracted with ether, the ether phase dried over anhydrous potassium carbonate and evaporated until beginning crystallization. The crystals were sucked off and dried. - 50 grams of 4-(2-acetyl-9-thioxanthenylidene)-1-methyl-piperidine were obtained melting at 125-127 degrees Centigrade.

1-(2,2,2-trichloroethoxycarbonyl)-4-(2-trifluoromethyl-6-fluoro-9-thioxanthenylidene)piperidine A mixture of 150 grams of 4-(2-trifluoromethyl-6-fluoro-9-thioxanthenylidene)-1-methylpiperidine, 100 grams of the 2,2,2-trichloroethylester of chloroformic acid and 1 liter of dry benzene were heated under reflux for 16 hours. After cooling the benzene solution was washed with dilute hydrochloric acid and dilute sodium hydroxide solution, dried over anhydrous potassium carbonate, filtered and evaporated in vacuum. Thereby somewhat impure 1-(2,2,2-trichloroethoxycarbonyl)-4-(2-trifluoromethyl-6-fluoro-9-thioxanthenylidene)-piperidine was obtained as an yellow oil which was used in the next step without further purification. Yield: 219 grams.

4-(2-trifluoromethyl-6-fluoro-9-thioxanthenylidene)-piperidine

The oil from the previous step was dissolved in 2.5 liters of 90% aqueous acetic acid; the solution was cooled to below 10 degrees Centigrade and while stirring were added 290 grams of zink which just before had been washed with dilute hydrochloric acid, dilute sodium hydroxide solution, water, ethanol and ether. The temperature rises by the heat of reaction to 15-20 degrees Centigrade. After 15 minutes the ice bath was removed and the stirring continued for further 3 hours. During this stage the temperature rised to 25-30 degrees Centigrade.

Thereafter the reaction mixture was filtered, washed with 90% aqueous acetic acid, evaporated in vacuum; water was added to the residue and aqueous ammonia added until basic reaction. The base which separated out was extracted with ether, the ether extract dried over anhydrous potassium carbonate and filtered. After evaporation the residue was crystalllized from ether-petroleum ether (1:1). 116 grams of 4-(2-trifluoromethyl-6-fluoro-9-thioxanthenylidene)-piperidine were obtained as white crystals which melted at 125-130 degrees Centigrade.

In corresponding manner were prepared the following starting materials of Formula II

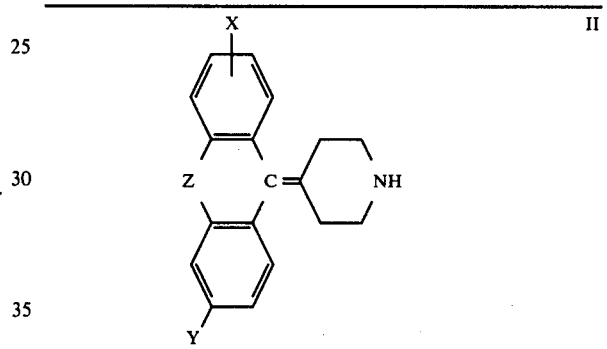

| X | Y | Z | MP in degrees Centigrade |
|---|---|---|---|
| 2-CF₃ | H | S | 116-118 |
| 2-Cl | H | S | 137-140 |
| 2-Cl | F | S | 135-136 |
| 2-S . CH₃ | H | S | 130-131 |
| 2-S . CH₃ | F | S | 128-132 |
| 3-F | H | S | 126-128 |
| 3-F | F | S | 148-150 |
| 2-CH₃ | F | S | 122-126 |
| 2-F | CH₃ | S | 125-127 |
| 2-SO₂N(CH₃)₂ | F | S | 196-198 |
| 2-SO₂CH₃ | H | S | 140-180 (amorph.) |
| 2-OCH₃ | F | S | 130-135 |
| 2-CF₃ | CH₃ | S | 135-137 |
| 2-CO . CH₃ | H | S | 115-117 |
| 2-OCH₃ | H | S | 122-124 |
| 2-S . CH₃ | F | O | 118-128 |
| 2-Cl | H | O | 140-145 |

EXAMPLE 2

(Method b))

1-(Trans-4-hydroxycyclohexylmethyl)-4-(2-trifluoromethyl-6-fluoro-9-thioxanthenylidene)piperidine In a separatory funnel were placed a solution of 23 grams of 4-(2-trifluoromethyl-6-fluoro-9-thioxanthenylidene)piperidine in 100 milliliters of toluene and a solution of 15 grams of potassium carbonate in 100 milliliters of ice water, whereupon trans-4-acetoxycyclohexanecarbonyl chloride prepared from 13 grams of corresponding acid (Helv.Chim.Acta 27, 793-800, 1944) was added and the mixture was shaken for 5 minutes. The aqueous phase was separated and discarded and the organic layer washed with dilute hydrochloric acid, dried over anhydrous potassium carbonate, filtered and evaporated in vacuum. The residue which consisted of somewhat impure 1-(trans-4-acetoxycyclohexanecarbonyl)-4-(2-trifluoromethyl-6-fluoro-9-thioxanthenylidene)piperidine was used without further purification in the reduction process and was dissolved in dry ether and added dropwise to a solution of 4 grams of lithiumaluminium hydride in dry ether. The reaction mixture was heated under reflux for 3 hours. Water was added with caution until the precipitate clotted. The ether phase was decanted, the precipitate washed thoroughly with ether, and the combined etherphases dried over anhydrous potassium carbonate, treated with active carbon and filtered. The major part of the ether was distilled off and 100 milliliters of petroleum ether were added. Upon cooling and standing 21 grams of 1-(trans-4-hydroxycyclohexylmethyl)-4-(2-trifluoromethyl-6-fluoro-9-thioxanthenylidene)-piperidine were obtained as a white crystalline substance melting at 144–146 degrees Centigrade.

In corresponding manner was prepared:

1-(trans-4-hydroxycyclohexylmethyl)-4-(2-chloro-9-thioxanthenylidene)-piperidine, MP: 185–190 degrees Centigrade.

1-(trans-2-hydroxycyclohexylmethyl)-4-(2-chloro-9-thioxanthenylidene) piperidine, MP: 96–103 degrees Centigrade.

1-(cis-4-hydroxymethylcyclohexylmethyl)-4-(2-chloro-9-thioxanthenylidene)-piperidine, MP: 85–90 degrees Centigrade.

1-(5-hydroxy-1,3-dioxan-2-yl)methyl-4-(2-chloro-9-thioxanthenylidene)-piperidine, MP: 160–162 degrees Centigrade.

1-(3,4-dihydroxycyclohexylmethyl)-4-(2-chloro-9-thioxanthenylidene)-piperidine, MP: 173–180 degrees Centigrade.

1-(trans-3-hydroxycyclohexylmethyl)-4-(2-trifluoromethyl-6-fluoro-9-thioxanthenylidene)-piperidine oxalate, MP: 155–157 degrees Centigrade.

1-(4-hydroxy-4-methylcyclohexylmethyl)-4-(2-trifluoromethyl-6-fluoro-9-thioxanthenylidene)-piperidine, MP: 80–90 degrees Centigrade.

1-(cis-2-hydroxycyclohexylmethyl)-4-(2-trifluoromethyl-6-fluoro-9-thioxanthenylidene)-piperidine, MP: 85–90 degrees Centigrade.

1-(3-trans-4-cis-dihydroxycyclohexylmethyl)-4-(2-trifluoromethyl-6-fluoro-9-thioxanthenylidene)-piperidine, amorphous substance.

1-(trans-4-hydroxycyclohexylmethyl)-4-(2-methylthio-6-fluoro-9-thioxanthenylidene)-piperidine, MP: 138–144 degrees Centigrade.

1-(trans-4-hydroxycyclohexylmethyl)-4-(2-methylthio-9-thioxanthenylidene)-piperidine, hydrochloride. MP: 285–287 degrees Centigrade.

1-(trans-4-hydroxycyclohexylmethyl)-4-(2-chloro-6-fluoro-9-thioxanthenylidene)-piperidine, MP: 178–180 degrees Centigrade.

1-(3-trans-4-cis-dihydroxycyclohexylmethyl)-4-(2-chloro-6-fluoro-9-thioxanthenylidene)-piperidine, MP: 110–120 degrees Centigrade.

1-(trans-4-hydroxycyclohexylmethyl)-4-(3,6-di-fluoro-9-thioxanthenylidene)-piperidine, MP: 154–156 degrees Centigrade.

1-(trans-4-hydroxycyclohexylmethyl)-4-(2-fluoro-6-methyl-9-thioxanthenylidene)-piperidine, MP: 158–162 degrees Centigrade.

1-(trans-4-hydroxycyclohexylmethyl)-4-(2-methyl-6-fluoro-9-thioxanthenylidene)-piperidine, MP: 181–185 degrees Centigrade.

1-(5-hydroxy-1,3-dioxan-2-yl)methyl-4-(2-trifluoromethyl-6-fluoro-9-thioxanthenylidene)-piperidine, MP: 138–140 degrees Centigrade.

1-(5-hydroxy-1,3-dioxan-2-yl)methyl-4-(2-methylthio-6-fluoro-9-thioxanthenylidene)-piperidine, MP: 129–131 degrees Centigrade.

1-(trans-4-hydroxycyclohexylmethyl)-4-(2-methoxy-6-fluoro-9-thioxanthenylidene)-piperidine, MP: 138–142 degrees Centigrade.

1-(trans-4-hydroxycyclohexylmethyl)-4-(2-trifluoromethyl-6-methyl-9-thioxanthenylidene)-piperidine, MP: 145–147 degrees Centigrade.

EXAMPLE 3

1-(Cis-4-hydroxycyclohexylmethyl)-4-(2-chloro-9-thioxanthenylidene)-piperidine (Method (a))

The starting material, cis-(1-mesyloxymethyl-4-hydroxy)cyclohexane, was prepared in the following way:

24 Grams of cis-4-hydroxycyclohexanemethanol were dissolved in a mixture of 70 milliliters of dry pyridine and 100 milliliters of chloroform. At a temperature of −20 degrees Centigrade were added 23 grams of mesyl chloride dropwise while stirring. The mixture was kept at −10 to −20 degrees Centigrade for 2 hours while stirring, whereupon the mixture was left standing over night at room temperature. The reaction mixture was then poured into ice-water, the chloroform layer was separated off and washed with dilute hydrochloric acid. The chloroform phase was then dried over anhydrous magnesium sulphate, filtered and evaporated. The residue was distilled in vacuum and 30 grams of cis-(1-mesyloxymethyl-4-hydroxy)cyclohexane were obtained as an oil boiling at 120–125 degrees Centigrade/1 mm Hg.

A mixture of 6 grams of 4-(2-chloro-9-thioxanthenylidene)piperidine, 4 grams of cis-(1-mesyloxymethyl-4-hydroxy)cyclohexane, 1.5 grams of finely crushed potassium carbonate and 25 milliliters of methylisobutylketone was heated under reflux for 5 hours while stirring. After cooling were added 200 milliliters of ether, and the organic phase was extracted with 5% aqueous methane sulphonic acid. The aqueous phase was made alkaline with aqueous ammonia, and the base which precipitated was extracted with ether. The etherphase was dried over anhydrous potassium carbonate, treated with active carbon and evaporated. The residue was crystallized from cyclohexane. Yield: 1.5 grams of 1-(cis-4-hydroxycyclohexylmethyl)-4-(2-chloro-9-thioxanthenylidene)piperidine, which melted at 100–103 degrees Centigrade.

In corresponding manner were prepared:

1-(2-(2-Oxazolidinone-3-yl)ethyl)-4-(2-chloro-9-thioxanthenylidene)piperidine, HCl. MP: 250–252 degrees Centigrade.

1-(5-hydroxy-1,3-dioxan-2-yl)methyl-4-(2-chloro-9-thioxanthenylidene)piperidine. MP: 160–162 degrees Centigrade.

1-(3-trans-4-cis-dihydroxycyclohexylmethyl)-4-(2-chloro-9-thioxanthenylidene)piperidine. MP: 173–180 degrees Centigrade.

1-(trans-4-hydroxycyclohexylmethyl)-4-(2-trifluoromethyl-6-fluoro-9-thioxanthenylidene)piperidine. MP: 144–146 degrees Centigrade.

1-(cis-4-hydroxycyclohexylmethyl)-4-(2-trifluoromethyl-6-fluoro-9-thioxanthenylidene)piperidine. MP: 149-152 degrees Centigrade.

1-(trans-3-hydroxycyclohexylmethyl)-4-(2-trifluoromethyl-6-fluoro-9-thioxanthenylidene)piperidine oxalate. MP: 155-157 degrees Centigrade.

1-(4-hydroxy-4-methylcyclohexylmethyl)-4-(2-trifluoromethyl-6-fluoro-9-thioxanthenylidene)piperidine. MP: 80-90 degrees Centigrade.

1-(2-cis-hydroxycyclohexylmethyl)-4-(2-trifluoromethyl-6-fluoro-9-thioxanthenylidene)piperidine. MP: 85-90 degrees Centigrade.

1-(3-Trans-4-cis-dihydroxycyclohexylmethyl)-4-(2-trifluoromethyl-6-fluoro-9-thioxanthenylidene)piperidine. Amorphous substance.

1-(1,3-Dioxan-4-ylmethyl)-4-(2-trifluoromethyl-6-fluoro-9-thioxanthenylidene)piperidine. MP: 151-153 degrees Centigrade.

1-(4-tetrahydropyranylmethyl)-4-(2-trifluoromethyl-6-fluoro-9-thioxanthenylidene)piperidine oxalate. MP: 138-140 degrees Centigrade.

1-(Trans-4-hydroxycyclohexylmethyl)-4-(2-methylthio-6-fluoro-9-thioxanthenylidene)piperidine. MP: 138-144 degrees Centigrade.

1-(Trans-4-hydroxycyclohexylmethyl)-4-(2-methylthio-9-thioxanthenylidene)piperidine, HCl. MP: 285-287 degrees Centigrade.

1-(Trans-4-hydroxycyclohexylmethyl)-4-(2-chloro-6-fluoro-9-thioxanthenylidene)piperidine. MP: 178-180 degrees Centigrade.

1-(2-(2-Oxazolidinon-3-yl)ethyl)-4-(2-chloro-6-fluoro-9-thioxanthenylidene)piperidine, HCl. MP: 248-250 degrees Centigrade.

1-(3-Trans-4-cis-dihydroxycyclohexylmethyl)-4-(2-chloro-6-fluoro-9-thioxanthenylidene)piperidine. MP: 110-120 degrees Centigrade.

1-(Trans-4-hydroxycyclohexylmethyl)-4-(3,6-difluoro-9-thioxanthenylidene)-piperidine. MP: 154-156 degrees Centigrade.

1-(2-Oxazolidinon-3-yl)ethyl)-4-(2-fluoro-6-methyl-9-thioxanthenylidene)-piperidine, HCl. MP: 243-246 degrees Centigrade.

1-(Trans-4-hydroxycyclohexylmethyl)-4-(2-fluoro-6-methyl-9-thioxanthenylidene)-piperidine. MP: 158-162 degrees Centigrade.

1-(2-(2-Oxazolidinon-3-yl)ethyl)-4-(2-methyl-6-fluoro-9-thioxanthenylidene)-piperidine, HCl. MP: 252-254 degrees Centigrade.

1-(Trans-4-hydroxycyclohexylmethyl)-4-(2-methyl-6-fluoro-9-thioxanthenylidene)-piperidine. MP: 181-185 degrees Centigrade.

1-(Trans-4-hydroxycyclohexylmethyl)-4-(2-bromo-6-fluoro-9-thioxanthenylidene)-piperidine.

1-(4-hydroxymethylcyclohexyl)-4-(2-trifluoromethyl-6-fluoro-9-thioxanthenylidene)piperidine. MP: 196-199 degrees Centigrade.

1-(4-hydroxycyclohexyl)-4-(2-trifluoromethyl-6-fluoro-9-thioxanthenylidene)piperidine, HCl. MP: 208-211 degrees Centigrade.

1-(2-Dioxolylmethyl)-4-(2-trifluoromethyl-6-fluoro-9-thioxanthenylidene)piperidine. MP: 137-139 degrees Centigrade.

1-Morpholinoethyl-4-(2-trifluoromethyl-6-fluoro-9-thioxanthenylidene)piperidine, 2HCl. MP: 300-305 degrees Centigrade.

1-(Cis-2-hydroxymethylcyclohexylmethyl)-4-(2-trifluoromethyl-6-fluoro-9-thioxanthenylidene)piperidine. MP: 85-100 degrees Centigrade.

1-(3-Tetrahydrofurylmethyl)-4-(2-trifluoromethyl-6-fluoro-9-thioxanthenylidene)piperidine oxalate. MP: 191-192 degrees Centigrade.

1-(2-(Cis-4-hydroxycyclohexyl)ethyl)-4-(2-trifluoromethyl-6-fluoro-9-thioxanthenylidene)piperidine maleate. MP: 147-150 degrees Centigrade.

1-(1-Methyl-4-piperidylmethyl)-4-(2-trifluoromethyl-6-fluoro-9-thioxanthenylidene)piperidine, 2HCl. MP: 322-324 degrees Centigrade.

1-(3-Trans-4-cis-dihydroxycyclohexylmethyl)-4-(2-bromo-9-thioxanthenylidene)piperidine oxalate. MP: 184-188 degrees Centigrade.

1-(Trans-4-hydroxycyclohexylmethyl)-4-(2-dimethylsulfamoyl-6-fluoro-9-thioxanthenylidene)piperidine, MP: 110-120 degrees Centigrade (amorph.)

1-(Trans-4-hydroxycyclohexylmethyl)-4-(2-methylsulfonyl-9-thioxanthenylidene)piperidine, MP: 70-85 degrees Centigrade (amorph.)

1-(Trans-4-hydroxycyclohexylmethyl)-4-(2-acetyl-9-thioxanthenylidene)piperidine oxalate hydrate, MP: 140-210 degrees Centigrade.

1-(2-(2-Imidazolidone-1-yl)ethyl)-4-(2-chloro-9-thioxanthenylidene)piperidine, MP: 205-206 degrees Centigrade.

1-(2-(2-Imidazolidone-1-yl)ethyl-4-(2-methylthio-6-fluoro-9-thioxanthenylidene)piperidine monohydrate, MP: 126-132 degrees Centigrade.

1-(1,3,4,5-tetrahydroxycyclohexylmethyl)-4-(2-methylthio-6-fluoro-9-thioxanthenylidene)piperidine, MP: 90-100 degrees Centigrade (amorph.)

1-(Trans-4-hydroxycyclohexylmethyl)-4-(2-methylthio-6-fluoro-9-xanthenylidene)piperidine hydrate, MP: 122-126 degrees Centigrade.

1-(Trans-4-hydroxycyclohexylmethyl)-4-(2-chloro-9-xanthenylidene)piperidine.

EXAMPLE 4

1-(Cis-4-hydroxycyclohexylethyl)-4-(2-trifluoromethyl-6-fluoro-9-thioxanthenylidene)-piperidine and maleate (Method b)

7.3 Grams of 4-(2-trifluoromethyl-6-fluoro-9-thioxanthenylidene)piperidine were dissolved in 50 milliliters of dry methylene chloride. Then 3.8 grams of cis-4-hydroxycyclohexane acetic cid (J.Am.Ch.Soc. 70, pg. 1898-99 (1948)) and 5 grams of dicyclohexylcarbodiimide were added. The mixture was heated at temperatures from 22 to 30 degrees Centigrade during which the dicyclohexylurea formed separated out and was then left standing overnight. The precipitate was filtered from the solution which was then evaporated, and the residue was dissolved in ether. The solution was washed with dilute hydrochloric acid, dried over anhydrous potassium carbonate, filtered and evaporated. The residue, which was an oil, wad dried by evaporation in vacuum with toluene and consisted of somewhat impure 1-(cis-4-hydroxycyclohexylmethylcarbonyl)-4-(2-trifluoromethyl-6-fluoro-9-thioxanthenylidene)-piperidine which was used without further purification in the next step. The oil was dissolved in dry ether, and 2 grams of lithium aluminum hydride were added in small portions. The mixture was heated under reflux for one hour. Then water was added dropwise until the precipitate formed clotted. The ether phase was decanted, the precipitate washed thoroughly with ether, the combined ether phases were dried over anhydrous potassium carbonate and treated with active carbon and filtered. The ether was evaporated, and 1-(cis-4-hydroxycyclohexylethyl)-4-(2-trifluoromethyl-6-fluoro-9-thioxanthenylidene)piperidine was obtained as a yellow oil.

Following solution in acetone and addition of maleic acid 8 grams of the maleate were obtained as white crystals which melted at 147–150 degrees Centigrade.

In corresponding manner were prepared:
1-(3-Trans-4-cis-dihydroxycyclohexylmethyl)-4-(2-methoxy-9-thioxanthenylidene)piperidine oxalate. MP: 235–236 degrees Centigrade.
1-(3,4,5-Cis-trihydroxycyclohexylmethyl)-4-(2-trifluoromethyl-6-fluoro9-thioxanthenylidene)piperidine oxalate. MP: 172–175 degrees Centigrade.
1-(3,4,5-Cis-trihydroxycyclohexylmethyl)-4-(2-methylthio-6-fluoro-9-thioxanthenylidene)piperidine hydrate. MP: 115–120 degrees Centigrade.
1-(3-Trans-4-cis-dihydroxycyclohexylmethyl)-4-(2-chloro-9-xanthenylidene)piperidine.

EXAMPLE 5

1-(Trans-4-hydroxycyclohexylmethyl)-4-(2-trifluoromethyl-6-fluoro-9-thioxanthenylidene)piperidine The starting material, 1-(4-cyclohexanone-carbonyl)-4-(2-trifluoromethyl-6-fluoro-9-thioxanthenylidene)-piperidine, was obtained in the following way:

25 Grams of 4-(2-trifluoromethyl-6-fluoro-9-thioxanthenylidene)piperidine were dissolved in 200 milliliters of dry methylene chloride. To this solution were added 12 grams of 4-cyclohexanone carboxylic acid and 16 grams of dicyclohexylcarbodiimide, whereby temperature in the reaction rose from 20 to 32 degrees Centigrade under simultaneous separation of dicyclohexylurea. The resulting mixture was then treated in the same manner as described in Example 4. The resulting 1-(4-cyclohexanonecarbonyl)-4-(2-trifluoromethyl-6-fluoro-9-thioxanthenylidene)-piperidine was obtained by crystallization from isopropyl ether and melted at 165–179 degrees Centigrade. Yield: 15 grams.

5 Grams of this amide were dissolved in dry ether and reduced with one gram of lithium aluminum hydride as described in Example 2, and the reaction mixture worked up as described there. 3.5 Grams of 1-(trans-4-hydroxycyclohexylmethyl)-4-(2-trifluoromethyl-6-fluoro-9-thioxanthenylidene)piperidine were obtained as a white crystalline substance which melted at 144–146 degrees Centigrade.

EXAMPLE 6

1-(4-Hydroxy-4-methylcyclohexylmethyl)-4-(2-trifluoromethyl-6-fluoro-9-thioxanthenylidene)piperidine (Method d)

14 Grams of 1-(4-cyclohexanonecarbonyl)-4-(2-trifluoromethyl-6-fluoro-9-thioxanthenylidene)-piperidine, obtained as described in Example 5, were dissolved in a mixture of 50 milliliters of dry tetrahydrofuran and 150 milliliters of dry ether. At 5–10 degrees Centigrade was added dropwise and while stirring a solution of methyl magnesium iodide in ether prepared from 6 grams of methyl iodide. Thereafter the reaction mixture was poured unto crushed ice, and the magnesium hydroxide which precipitated was dissolved by addition of dilute hydrochloric acid. The ether phase was washed once with dilute hydrochloric acid, dried over anhydrous potassium carbonate, filtered and evaporated. The resulting oil was reduced with 3 grams of lithium aluminium hydride without further purification as described in Example 2. The base formed by the reduction was purified by solution in 5% aqueous methane sulphonic acid, the solution washed with ether and the base precipitated with dilute aqueous ammonia. The base was extracted with ether, the ether phase dried over anhydrous potassium carbonate, treated with active carbon and evaporated, finally in vacuum. 12 Grams of 1-(4-hydroxy-4-methylcyclohexylmethyl)-4-(2-trifluoromethyl-6-fluoro-9-thioxanthenylidene)-piperidine were thereby obtained as an almost white amorphous substance which melted at 80–90 degrees Centigrade.

EXAMPLE 7

1-(4-Hydroxymethylcyclohexyl)-4-(2-trifluoromethyl-9-thioxanthenylidene)-piperidine (Method d)

The starting material, the methyl ester of 1-(4-carboxycyclohexyl)-4-(2-trifluoromethyl-9-thioxanthenylidene)piperidine, was obtained in the following way:

11.6 Grams of 4-(2-trifluoromethyl-9-thioxanthenylidene)piperidine were dissolved in 30 milliliters of dry methanol, and to the solution were added 5.5 grams of 4-cyclohexanonecarboxylic acid and 1.5 grams of sodium cyano borohydride, whereupon the mixture was left standing overnight. The amino acid formed was esterified by addition of a mixture of 200 milliliters of dry methanol and 20 milliliters of concentrated sulphuric acid and heating for 3 hours under reflux. The mixture was poured into ice-water, aqueous ammonia added to alkaline reaction and extracted with ether. The ether-solution contained the methyl ester of 1-(4-carboxycyclohexyl)-4-(2-trifluoromethyl-9-thioxanthenylidene)piperidine formed and was reduced after drying without further purification using 1.5 grams of lithium aluminium hydride. The reaction mixture was worked up as described in Example 2, and 5.5 grams of 1-(4-hydroxymethylcyclohexyl)-4-(2-trifluoromethyl-9-thioxanthenylidene)piperidine were obtained by crystallization from ether as white crystals which melted at 193–197 degrees Centigrade.

EXAMPLE 8

1-(4-Hydroxycyclohexyl)-4-(2-trifluoromethyl-6-fluoro-9-thioxanthenylidene)-piperidine and its hydrochloride In the same manner as described in Example 7 a mixture of 2.2 grams of 4-(2-trifluoromethyl-6-fluoro-9-thioxanthenylidene)piperidine and 8.5 grams of benzoyloxycyclohexanone in 30 milliliters of dry methanol adjusted to pH 5 were reduced with 1.5 grams of sodium cyanoborohydride and the resulting 1-(4-benzoyloxy cyclohexyl)-4-(2-trifluoromethyl-6-fluoro-9-thioxanthenylidene)-piperidine reduced with lithium aluminium hydride as described in Example 2.

8.4 Grams of the hydrochloride of 1-(4-hydroxycyclohexyl)-4-(2-trifluoromethyl-6-fluoro-9-thioxanthenylidene)-piperidine were obtained as white crystals which melted at 208–211 degrees Centigrade.

EXAMPLE 9

1-(Cis-2-hydroxymethylcyclohexylmethyl)-4-(2-trifluoromethyl-6-fluoro-9-thioxanthenylidene)piperidine and its oxalate A mixture of 7.3 grams of 4-(2-trifluoromethyl-6-fluoro-9-thioxanthenylidene)piperidine, 3.3 grams of cis-hexahydrophthalic acid anhydride and 30 milliliters of toluene was heated under reflux for 5 hours. After cooling 200 milliliters of dry ether were added and the mixture reduced with 2 grams of lithium aluminium hydride in the same manner as described in Example 2.

7.8 Grams of the oxalate of 1-(cis-2-hydroxymethyl-cyclohexylmethyl)-4-(2-trifluoromethyl-6-fluoro-9-thioxanthenylidene)piperidine were obtained by crystallization from acetone as white crystals which melted at 155–156 degrees Centigrade.

EXAMPLE 10

The decanoic acid ester of 1-(trans-4-hydroxycyclohexylmethyl)-4-(2-chloro-9-thioxanthenylidene)-piperidine 6 Grams of 1-(trans-4-hydroxycyclohexylmethyl)-4-(2-chloro-9-thioxanthenylidene)-piperidine were dissolved in 50 milliliters of dry pyridine. 4 Grams of decanoylchloride were added and the mixture left standing for 18 hours at room temperature. The mixture was poured into 1 liter of water and extracted with 100 milliliters of isopropyl ether. The etherphase was washed with water, dried over anhydrous potassium carbonate, filtered and evaporated to about 15 milliliters. By addition of petroleum ether and cooling 8 grams of the decanoic acid ester of 1-(trans-4-hydroxycyclohexylmethyl)-4-(2-chloro-9-thioxanthenylidene)-piperidine were obtained as a white crystalline substance which melted at 100–108 degrees Centigrade.

In the same manner was prepared:

The decanoic acid ester of 1-(trans-4-hydroxycyclohexylmethyl)-4-(2-trifluoromethyl-6-fluoro-9-thioxanthenylidene)-piperidine. Melting point of the hydrochloride: 210–212 degrees Centigrade.

The palmitic acid ester of 1-(trans-4-hydroxycyclohexylmethyl)-4-(2-trifluoromethyl-6-fluoro-8-thioxanthenylidene)-piperidine.

The behenic acid ester of 1-(trans-4-hydroxycyclohexylmethyl)-4-(2-trifluoromethyl-6-fluoro-9-thioxanthenylidene)-piperidine.

EXAMPLE 11

1-(4-Oxocyclohexylmethyl)-4-(2-trifluoromethyl-6-fluoro-9-thioxanthenylidene)piperidine and its hydrochloride A mixture of 13 grams of 1-(trans-4-hydroxycyclohexylmethyl)-4-(2-trifluoromethyl-6-fluoro-9-thioxanthenylidene)piperidine, 80 milliliters of cyclohexanone, 300 milliliters of dry toluene and 4 grams of aluminiumisopropoxide was heated to boiling, and in the course of one hour 200 milliliters of liquid were distilled off. The reaction mixture was cooled, water was added and the aluminium hydroxide which precipitated was sucked off. The organic layer was extracted with dilute hydrochloric acid, the acid solution made alkaline and extracted with ether. The ether phase was dried over anhydrous potassium carbonate and evaporated, the residue was dissolved in acetone, and by addition of dry hydrogen chloride in ether the hydrochloride 1-(4-oxocyclohexylmethyl)-4-(2-trifluoromethyl-6-fluoro-9-thioxanthenylidene)piperidine was obtained as white crystals which melted at 232–235 degrees Centigrade. Yield: 4.5 grams.

EXAMPLE 12

1-(Trans-4-aminocyclohexylmethyl)-4-(2-chloro-9-thioxanthenylidene)piperidine and its acetylderivative and mesylderivative 4-(2-Chloro-9-thioxanthenylidene)piperidine was reacted with trans-4-(2,2,2-trichloroethoxycarbonylamino)cyclohexanecarbonyl chloride as described in Example 2 (Method b). 1-(Trans-4-(2,2,2-trichloroethoxycarbonylamine)cyclohexanecarbonyl)-4-(2-chloro-9-thioxanthenylidene)piperidine was thereby obtained as a yellow oil.

The yellow oil was reduced with activated zink in acetic acid according to the procedure described for 4-(2-trifluoromethyl-6-fluoro-9-thioxanthenylidene)-piperidine in Example 1. 1-(Trans-4-aminocyclohexylcarbonyl)-4-(2-chloro-9-thioxanthenylidene)piperidine was thereby obtained as a white crystalline substance melting at 230–260 degrees Centigrade after recrystallization from toluene.

This substance was then reduced with lithium aluminium hydride as described in example using dry tetrahydrofuran instead of ether. 1-(Trans-4-aminocyclohexylmethyl)-4-(2-chloro-9-thioxanthenylidene)piperidine was thus obtained as a white crystalline substance melting at 128–135 degrees Centigrade.

The starting material, trans-4-(2,2,2-trichloroethoxycarbonylamino)cyclohexanecarbonyl chloride, was prepared from trans-4-aminocyclohexane carboxylic acid by a Schotten-Baumann reaction with the 2,2,2-trichloroethylester of chloroformic acid followed by reflux for three hours with 50% excess of thionyl chloride. It was obtained as a yellow oil.

In corresponding manner was prepared:

1-(Trans-4-aminocyclohexylmethyl)-4-(2-trifluoromethyl-6-fluoro-9-thioxanthenylidene)piperidine. MP: 100–102 degrees Centigrade.

The acetyl derivative of the last mentioned amine was prepared to conventional manner by treatment of the amine with acetic anhydride in toluene and melted at 215–217 degrees Centigrade.

The corresponding mesyl derivative was prepared by dissolving 6 grams of the amine in 50 milliliters of dichloromethane, adding a solution of 30 grams of potassiumcarbonate in 100 milliliters of water, and, while stirring vigorously, adding dropwise at zero degrees Centigrade 10 grams of mesyl chloride. The organic phase was dried over anhydrous potassium carbonate and filtered.

By addition of ether 3 grams of the mesylderivative were obtained, melting at 170–180 degrees Centigrade.

The novel xanthones and thioxanthones used as starting materials for the preparation of the compounds of Formula II were prepared as follows:

2-Methylthio-6-fluoro-9-thioxanthone

375 Grams of 2-(p-methylthiophenylthio)-4-fluoro-benzoic acid (Collec.Czech.Chem.Commun. 40, pg. 3523 (1975)) were heated with 2.7 kilograms of polyphosphoric acid while stirring for 3 hours at 140 degrees Centigrade. The mixture was cooled to 110 degrees Centigrade and poured into ice-water. The precipitate was sucked off, suspended in aqueous ammonia and sucked off again.

After recrystallization from pyridine 200 grams of 2-methylthio-6-fluoro-9-thioxanthone was obtained as a yellow crystalline substance which melted at 135–138 degrees Centigrade.

2-Methyl-6-fluoro-9-thioxanthone

A mixture of 110 grams of 2-bromo-4-fluoro-benzoic acid, 63 grams of 4-methylthiophenol, 100 grams of potassium carbonate, 250 milliliters of dimethylformamide, 2 grams of active copper and 1 gram of cuproiodide was heated while stirring under reflux for 16 hours. The mixture was poured into water, undissolved substance sucked off and the resulting solution made acid with hydrochloric acid. The precipitate was sucked off and dissolved in ether. The ether solution was dried over anhydrous magnesium sulphate, treated with active carbon and most of the ether evaporated. By addition of petroleum ether and cooling 81 grams of 2-(4-methylphenylthio)-4-fluorobenzoic acid were obtained as white crystals which melted at 190–200 degrees Centigrade.

This acid was heated at 50–60 degrees Centigrade with 650 milliliters concentrated sulphuric acid while stirring, whereupon the mixture was poured unto crushed ice. The precipitate was sucked off, suspended in aqueous ammonia and sucked off again. After recrystallization from ethanol 41 grams of 2-methyl-6-fluoro-9-thioxanthone were obtained as pale yellow crystals which melted at 159–165 degrees Centigrade.

2-Fluoro-6-methyl-9-thioxanthone

A mixture of 80 grams of 2-bromo-4-methylbenzonitrile, 52 grams of 4-fluorothiophenol, 56 grams of potassium carbonate, 200 milliliters of dimethylformamide and 1 grams of active copper was heated while stirring. At 90 degrees Centigrade a reaction started resulting in rise of temperature and separation of potassium bromide. The mixture was heated under reflux for one hour, cooled and poured into water. The precipitate was sucked off and dissolved in ether. The ether solution was washed with dilute sodium hydroxide solution, dried over anhydrous magnesium sulphate, treated with active carbon and the ether evaporated. The residue was recrystallized from ethanol, and 93 grams of 2-(4-fluorophenylthio)-4-methylbenzonitrile were obtained as white crystals which melted at 93–96 degrees Centigrade.

This nitrile was heated under reflux for 16 hours with a solution of 85 grams of potassium hydroxide in 600 milliliters of 80% ethanol. The mixture was poured into water and made acid with hydrochloric acid. 96 Grams of 2-(4-fluorophenylthio)-4-methylbenzoic acid crystallized thereby as a white crystalline substance which melted at 185–193 degrees Centigrade.

By treatment with concentrated sulphuric acid as described in the previous example, 58 grams of 2-fluoro-6-methyl-9-thioxanthone were obtained after recrystallization from ethanol as yellow crystals which melted at 166–170 degrees Centigrade.

2-Methoxy-6-fluoro-9-thioxanthone

This substance is prepared as described for 2-methyl-6-fluoro-9-thioxanthene, and the intermediate 2-(p-methoxyphenylthio)-4-fluoro-benzoic acid melts at 195–204 degrees Centigrade.

This substance yields by heating with polyphosphoric acid, as described above for 2-methylthio-6-fluoro-9-thioxanthone, 2-methoxy-6-fluoro-9-thioxanthone, which melts at 170–174 degrees Centigrade.

2-Trifluoromethyl-6-methyl-9-thioxanthone

A mixture of 40 grams of sodium hydroxide, 1 liter of ethanol and 124 grams of m-thiocresol was stirred until the sodium hydroxide was dissolved.

206 Grams of 2-chloro-5-trifluoromethylbenzonitrile were then added while stirring and under reflux. The mixture was then heated under reflux for two hours. After cooling 100 grams of potassium hydroxide were added and the mixture heated under reflux overnight. The mixture was then diluted with 3 liters of water and made acid with hydrochloric acid. The precipitate was filtered off and consisted of 2-(3-methylphenylthio)-5-trifluoromethylbenzoic acid. Yield: 240 grams.

This was then treated with sulphuric acid as described for 2-methyl-6-fluoro-9-thioxanthone. The resulting substance consisted mainly of 2-trifluoro-6-methyl-9-thioxanthone with some 2-trifluoromethyl-8-methyl-9-thioxanthone. When boiling this mixture with acetone the more soluble 8-methyl-compound will go into solution. The remaining 2-trifluoromethyl-6-methyl-9-thioxanthone was obtained as a yellow crystalline substance, which melts at 174–178 degrees Centrigrade. Yield: 80 grams.

2-Methylthio-6-fluoro-9-xanthone

A mixture of 36.8 grams of 5-methylthio salicylic acid, 38 grams of 3-bromofluorobenzene, 32 grams of anhydrous potassium carbonate and 3 grams of copper powder in 100 milliliters of dimethylformamide was heated to boiling, and 25 milliliters of liquid were distilled off until the temperature in the mixture reached 150 degrees Centigrade. 35 Grams of 3-bromofluorobenzene were then added, and the mixture was refluxed overnight. 200 Milliliters of water were added, and the warm reaction mixture was filtered with charcoal. The filtrate was extracted once with diethylether and made acid with 6 N hydrochloric acid. The precipitate was sucked off and taken up in 500 milliliters of diethylether, dried over anhydrous magnesium sulphate and concentrated. The crystals were sucked off and dried. 26 Grams of 2-(3-fluoro-phenoxy)-5-methylthio-benzoic acid melting at 137–140 degrees Centigrade were obtained.

The 26 grams of this acid were added to 225 grams of polyphosphoric acid while stirring and the mixture heated on a steam bath for three hours. The reaction mixture was poured onto ice, filtered and taken up in 250 milliliters of methylene chloride. The organic phase was washed with 25% aqueous ammonia and water, dried over anhydrous magnesium sulphate and evaporated to give 20 grams of a mixture of 6- and 8-fluoro-2-methylthio-9-xanthones.

Three recrystallizations from 16 milliliters of pyridine yielded 6 grams of pure 2-methylthio-6-fluoro-9-xanthone which melted at 113–116 degrees Centigrade.

The pharmacological testing of the novel xanthones and thioxanthenes of Formula I consisted of standard and reliable tests.

There the results with salts were compared with the results obtained with the free base it was found that the effect was the same as that obtained with the equivalent amount of free base.

The tests may be described as follows:

Methylphenidate antagonism (ED50 mg/kg i.p.)

Perspex observation cages without bottom and lid, consisting of 5 sections each measuring 12×25×30 cm. White corrugated paper. Mice, male, 18–25 g.

Dosage and procedure

The test substance is given i.p. in the doses 0, ⅛, 1/32 and 1/128 of the determined "i.p. LD50". 3×2 mice are used for each dose level. Two or 24 hours after injection of test substance, methylphenidate, 60 mg/kg, is injected s.c. After administration of methylphenidate the mice are placed in the observation cages, 2 in each cage, where they remain for exactly 1 hour. The cages are placed on corrugated paper, the corrugations facing upwards. It is examined whether the mice have been biting the corrugated paper or not. If not, the substance has had an antagonistic effect. If one or more of the control pairs have not been biting, the test has to be repeated on a new set of mice.

The result is stated in fractions: 0/3, ⅓, ⅔, and 3/3 where 0, 1, 2 and 3 are the number of pairs which have not been biting on receipt of the dose in question.

The results are calculated as the dose (ED$_{50}$), which causes antagonism in 50% of the test animals.

Amphetamine antagonism (ED$_{50}$ mg/kg i.p.)

Perspex observation cages without bottom and lid, consisting of 5 sections each measuring 12×25×30 cm. White corrugated paper. Rats, male, 230–270 g.

Dosage and procedure

The test substance is given i.p. in a reasonable dose based on the determined LD$_{50}$. Two or 24 hours later an intravenous injection of amphetamine sulphate 13.6 mg/kg (10 mg/kg amphetamine base) is given, after which the rats are placed individually in the cages. The cages are placed on white corrugated paper. Five rats are used for each dose level. Observations are made after 55 minutes and 65 minutes—observation time: 1 minute. The animals are observed for stereotypy (movements of the head, compulsive gnawing). If no stereotypy is demonstrated the substance has had an antagonistic effect. If the compound has full antagonistic effect another group of rats is used at a lower dose. If the compound shows no effect a higher dose is used. The results is stated as fractions: 0/5, 1/5, 2/5, 3/5, 4/5 and 5/5, where 0, 1, 2, 3, 4 and 5 indicate the number of rats which have not shown stereotypy at the dose in question. The results are calculated as ED$_{50}$ in mg/kg.

Catalepsy wire mesh, rat, max. (ED$_{50}$ mg/kg s.c.)

A vertical wire netting (50 cm×49 cm). The meshes (openings) of the netting are square (1 cm×1 cm). The wire diameter is 2 mm. Stop watch. Rats, male, 180–200 g.

Dosage and procedure

The animals are labeled and used in groups of five. The test substance is injected subcutaneously (s.c.) (5 ml/kg) at 4 dose levels selected from the fixed dose scale.

The animals are placed in the middle of the vertical wire netting 60, 120, 180, 240, 300 and 360 minutes after injection of the test compound. The animals are considered cataleptic when they remain immobile during a period of 15 seconds. This cataleptic reaction is designated +. If the rats are "atonic" and passively slide down the wire mesh they are considered not cataleptic. If the animals climb up and down the wire mesh they are nor cataleptic. In both situations the designation—is used.

The results are recorded in fractions: 0/5, 1/5, 2/5, 3/5, 4/5 and 5/5, where 0, 1, 2, 3, 4 and 5 are the number of rats with designation+at the time where the dose in question possessed the strongest effect within the first 6 hours.

The compounds tested will appear from the following table:

TABLE 1

| Code Number | X | Y | n | R | Z |
|---|---|---|---|---|---|
| Lu 14-047 | 2-Cl | H | 1 | 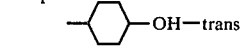 —⟨⟩—OH—trans | S |
| Lu 15-014 | 2-Cl | H | 1 | 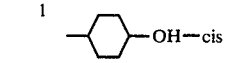 —⟨⟩—OH—cis | S |
| Lu 14-106 | 2-Cl | H | 2 | 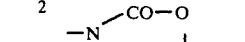 —N⟨CO—O⟩ | S |
| Lu 14-140 | 2-Cl | H | 1 | 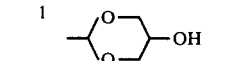 —⟨O—O⟩—OH | S |
| Lu 15-041 | 2-Cl | H | 1 | 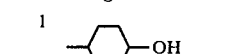 —⟨⟩—OH, OH | S |
| Lu 13-135 | 2-CF$_3$ | F | 1 | 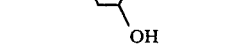 —⟨⟩—OH—trans | S |
| Lu 15-013 | 2-CF$_3$ | F | 1 | 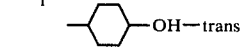 —⟨⟩—OH—cis | S |

TABLE 1-continued
| Code Number | X | Y | n | R | Z |
|---|---|---|---|---|---|
| Lu 15-030 | 2-CF$_3$ | F | 1 |  | S |
| Lu 15-048 | 2-CF$_3$ | F | 1 |  | S |
| Lu 15-038 | 2-CF$_3$ | F | 1 |  | S |
| Lu 15-052 | 2-CF$_3$ | F | 1 |  | S |
| Lu 14-130 | 2-CF$_3$ | F | 1 |  | S |
| Lu 15-131 | 2-CF$_3$ | F | 1 |  | S |
| Lu 14-116 | 2-SCH$_3$ | F | 1 |  | S |
| Lu 15-019 | 2-SCH$_3$ | H | 1 |  | S |
| Lu 14-114 | 2-Cl | F | 1 |  | S |
| Lu 14-117 | 2-Cl | F | 2 |  | S |
| Lu 15-070 | 2-Cl | F | 1 |  | S |
| Lu 15-062 | 3-F | F | 1 |  | S |
| Lu 14-062 | 2-F | CH$_3$ | 2 |  | S |
| Lu 14-090 | 2-F | CH$_3$ | 1 |  | S |
| Lu 14-070 | 2-CH$_3$ | F | 2 |  | S |
| Lu 14-082 | 2-CH$_3$ | F | 1 |  | S |
| Lu 16-107 | 2-SO$_2$N(CH$_3$)$_2$ | F | 1 |  | S |
| Lu 16-066 | 2-SO$_2$CH$_3$ | H | 1 |  | S |
| Lu 16-052 | 2-OCH$_3$ | F | 1 |  | S |
| Lu 16-014 | 2-CF$_3$ | CH$_3$ | 1 |  | S |
| Lu 15-121 | 2-CF$_3$ | F | 1 |  | S |

TABLE 1-continued

| Code Number | X | Y | n | R | Z |
|---|---|---|---|---|---|
| Lu 16-105 | 2-Cl | H | 2 |  | S |
| Lu 16-104 | 2-CF$_3$ | F | 2 |  | S |
| Lu 15-089 | 2-CF$_3$ | F | 1 | 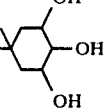 | S |
| Lu 15-119 | 2-SCH$_3$ | F | 1 | —OH—trans | O |
| Lu 16-088 | 2-CF$_3$ | F | 1 | =O | S |
| Lu 16-042 | 2-CF$_3$ | F | 1 | —NH$_2$—trans | S |
| Lu 16-081 | 2-Cl | H | 1 | —NH$_2$—trans | S |
| Lu 16-043 | 2-CF$_3$ | F | 1 | —NHOC.CH$_3$—trans | S |
| Lu 16-049 | 2-CF$_3$ | F | 1 | —NHO$_2$S.CH$_3$—trans | S |

As reference substances were used the following neuroleptic drugs designated by their INN-names (International Nonproprietary Names): flupentixol, clopenthixol, chlorprothixene, fluphenazine, chlorpromazine, haloperidol and clozapine. Moreover the cis- (z)-isomer of 2-trifluoromethyl-6-fluoro-9-(3-(4-(2-hydroxyethyl)-1-piperidyl)propylidene)-thioxanthene; INN-name; piflutixol.

TABLE 2

| | Methylphenidate antagon | | Amphetamine | | Remarks |
| Substance | 2 h | 24 h | antagon | Catalepsy | Duration |
|---|---|---|---|---|---|
| Lu 14-047 | 0.59 | >20 | 0.32 | 3.5 | short acting, strong |
| Lu 15-014 | 0.20 | >10 | | 2.5 | " |
| Lu 14-106 | 0.51 | >40 | 1.0 | 6.6 | " |
| Lu 14-140 | 0.77 | >40 | | | " |
| Lu 15-041 | 0.62 | 3.6 | <0.31 | | moderately long acting, strong |
| Lu 13-135 | 0.32 | 0.19 | 0.32 | 0.4 | very long acting, strong |
| Lu 15-013 | 0.63 | 0.10 | 0.76 | 1.2 | long acting, strong |
| Lu 15-030 | 0.28 | 0.05 | 0.88 | 0.39 | long acting, very strong |
| Lu 15-048 | 1.30 | 0.13 | <0.31 | | long acting, strong |
| Lu 15-138 | 1.30 | 0.15 | 1.7 | | " |
| Lu 15-052 | 0.32 | 0.06 | 0.9 | 0.026 | " |
| Lu 14-130 | 0.77 | 0.70 | 0.62 | 2.8 | long acting, moderately strong |
| Lu 15-031 | 0.52 | 0.55 | 1.3 | | " |
| Lu 14-116 | 0.44 | 0.38 | 0.28 | 0.58 | long acting, strong |
| Lu 15-019 | 0.77 | >40 | 0.59 | 0.60 | short acting, moderately strong |
| Lu 14-114 | 0.1 | 6.6 | 0.35 | | short acting, strong |
| Lu 14-117 | 0.21 | 29 | 0.34 | 1.0 | " |
| Lu 15-070 | 0.51 | 0.5 | | | moderately long acting, moderately strong |
| Lu 15-062 | 0.77 | >10 | 0.85 | | short acting, moderately strong |
| Lu 14-062 | 0.51 | >40 | | | " |
| Lu 14-090 | 1.25 | 32 | | | " |
| Lu 14-070 | 0.32 | >40 | 1.3 | 1.8 | " |
| Lu 14-082 | 0.79 | >10 | | | " |
| Lu 16-107 | 1.9 | 0.76 | | 0.28 | long acting, moderately strong |
| Lu 16-066 | 0.73 | >10 | | 0.25 | short acting, moderately strong |
| Lu 16-052 | 0.31 | 29 | 0.56 | 0.23 | " |
| Lu 16-014 | 0.31 | 1.9 | 1.0 | 0.97 | long acting moderately strong |
| Lu 15-121 | 2.2 | 0.31 | 10.0 | >10 | long acting, strong, weak catalep. |
| Lu 16-105 | 0.16 | 28 | 1.2 | 0.38 | short acting, strong |
| Lu 16-104 | 0.06 | 1.5 | 0.15 | 0.11 | relatively short acting, strong |
| Lu 15-089 | 0.32 | 0.32 | 1.8 | 2.7 | relatively short acting, moderately strong |
| Lu 15-119 | 0.09 | 0.11 | 0.56 | 0.08 | very strong, long acting. |
| Lu 16-088 | 0.77 | 0.06 | 0.30 p.o. | 0.81 | strong, long acting |
| Lu 16-042 | 1.2 | 0.17 | 2.5 p.o. | 3.3 | " |
| Lu 16-081 | 0.5 | ~10 | | | moderately strong, short acting. |
| Lu 16-043 | >10 | 0.42 | | >20 | relatively strong, long acting |
| Lu 16-049 | 1.0 | 0.49 | 2.5 p.o. | 1.7 p.o. | moderately strong, long acting. |

TABLE 2-continued

| Substance | Methylphenidate antagon 2 h | 24 h | Amphetamine antagon | Catalepsy | Remarks Duration |
|---|---|---|---|---|---|
| flupentixol | 0.20 | >20 | 0.69 | 0.25 | short acting, strong |
| clopenthixol | 1.20 | | 0.77 | 0.95 | short acting, moderately strong |
| chlorprothixene | 0.71 | >20 | 6.1 | 4.0 | " |
| fluphenazine | 0.04 | 3.6 | 0.08 | 0.099 | short acting, very strong |
| chlorpromazine | 4.0 | 20 | 7.1 | 5.6 | short acting, moderately strong |
| haloperidol | 0.06 | | 0.14 | 0.21 | short acting, very strong |
| clozapine | >160 | | >40 | 85 | short acting, weak |
| piflutixol | 0.03 | 0.03 | | 0.05 | 48–72h $LD_{50}$ p.o. in male rats after 1 week 1.5mg/kg |

From Table 2 it appears that among the compounds having a substituent in the 2-position and a fluorine atom or methyl group at position 6 one finds the most long acting and also strongest acting.

On the other hand, they also show a comparatively high cataleptic activity, which indicates extrapyramidal symptoms. The compounds wherein Y is hydrogen are as general rule rather short acting but, on the other hand, they often show a more favourable ration between the cataleptic activity and the methylphenidate antagonism.

Among the compounds wherein R is a cyclohexyl group having from one to three hydroxyl groups one finds some of the most promising compounds. Especially remarkable are Lu 13-135, Lu 15-030, Lu 15-052 and Lu 15-119 in that they are very strong and long acting but they also have a cataleptic activity. Interesting is Lu 15-121 in that it seems to be strong, long acting and at the same time having no cataleptic activity.

When comparing the most long acting and strongest of the compounds of Formula I with piflutixol, which is the most patent and at the same time the most long acting neuroleptic so far known, it has been found that they cause much less sedation. Moreover, they have much stronger anticholinergic effects than the compounds known from U.S. Pat. No. 4,042,695, and this is considered an indication of a lower degree of undesired extrapyrimidal side effects.

The acute toxicity, as measured by $LD_{50}$ in male rats following peroral administration, is much lower for Lu 13-135 when compared with piflutixol one week after administration. The figure for Lu 13-135 is > 60 mg/kg against 1.5 mg/kg for piflutixol. The considerably greater toxicity of piflutixol being attributed mainly to the aforementioned very strong sedative effects.

The compounds of Formula I and the non-toxic acid addition salts thereof may be administered to animals such as dogs, cats, horses sheeps or the like, including human beings, both orally and parenterally, and may be used for example in the form of tablets, capsules, powders, syrups or in the form of the usual sterile solutions for injection. Results upon administration to human beings have been very gratifying.

Most conveniently the compounds of Formula I are administered orally in unit dosage form such as tablets or capsules, each dosage unit containing a non-toxic acid addition salt of one of the said compounds in an amount of from about 0.05 to about 50 mg, most preferably, however, from about 1 to 10 mg, calculated as the free amine, the total daily dosage usually ranging from about 0.5 to about 300 mg. The exact individual dosages as well as daily dosages in a particular case will, of course, be determined according to established medical principles under the direction of a physician.

When preparing tablets, the active ingredient is for the most part mixed with ordinary tablet adjuvants such as corn starch, potato starch, talcum, magnesium stearate, gelatine, lactose, gums, or the like.

When the compound of Formula I is an ester, preferably a decanoic acid ester, palmitic acid ester or a behenic acid ester, the composition may advantageously be an oily solution for injection, and such solutions often have a very prolonged effect when compared with the corresponding unesterified compound.

Typical examples of formulas for composition containing 1-(trans-4-hydroxycyclohexylmethyl)-4-(2-trifluoromethyl-6-fluoro-9-thioxanthenyliden)-piperidine (called Lu 13-135 for short) as the active ingredient are as follows:

(1) Tablets containing 0.1 milligram of Lu 13-135 calculated as the free base:
Lu 13-135: 0.1 mg
lactose: 37 mg
potato starch: 74 mg
gelatine: 2 mg
talcum: 8 mg (2) Solution for injection containing per ml:
Lu 13-135: 0.2 mg
sodium chloride: 9.0 mg
sterile water ad: 1 ml (3) Syrup containing per milliliter:
Lu 13-135: 0.2 mg
methyl-paraben: 1.0 mg
propyl-paraben: 0.1 mg
saccharose: 400 mg
water: ad: 1 ml (4) Capsules containing per capsule:
Lu 13-135: 1 mg
lactose: 40 mg
magnesium stearate: 0.5 mg Any other pharmaceutical tableting adjuvants may be used provided that they are compatible with the active ingredient, and additional compositions and dosage forms may be similar to those presently used for neuroleptics, such as thiothixene, clopenthixol or flupenthixol. Also combinations of the compounds of Formula I as well as their non-toxic acid salts with other active ingredients, especially other neuroleptics, thymoleptics, tranquilizers or the like, fall within the scope of the present invention.

As previously stated, when isolating the compounds of Formula I in the form of an acid addition salt the acid is preferably selected so as to contain an anion which is non-toxic and pharmacologically acceptable, at least in usual therapeutic doses. Representative salts which are included in this preferred group are the hydrochlorides, hydrobromides, sulphates, acetates, phosphates, nitrates, methanesulphonates, ethane-sulphonates, lactates, citrates, tartrates or bitartrates, embonates and maleates of the amines of Formula I. Other acids are likewise suitable and may be employed if desired. For example; fumaric, benzoic, ascorbic, succinic, salicylic, bismethylenesalicylic, propionic, gluconic, malic, malonic, mandelic, cannamic, citraconic, stearic, palmitic, itaconic, glycolic, benzenesulphonic, and sulphamic acids may also be employed as acid addition saltforming acids.

When it is desired to isolate a compound of the invention in the form of the free base, this may be done according to conventional procedure as by dissolving the isolated or unisolated salt in the water, treating with a suitable alkaline material, extracting the liberated free base with a suitable organic solvent drying the extract and evaporating to dryness or fractionally distilling to effect isolation of the free basic amine.

The invention also comprises a method for the alleviation, palliation, mitigation or inhibition of the manifestations of certain physiological-psychological abnormalies of animals by administering to a living animal body, including human beings, an adequate quantity of a compound of Formula I or a non-toxic acid addition salt thereof. An adequate quantity would be from about 0.001 mg to about 1 mg per kg of body weight in each unit dosage, and from about 0.003 milligrams to about 3 milligrams/kg of body weight per day.

It is to be understood that the invention is not limited to the exact details of operation or exact compound or compositions shown and described, as obvious modifications and equivalents will be apparent to one skilled in the art.

We claim:

1. A compound of the formula:

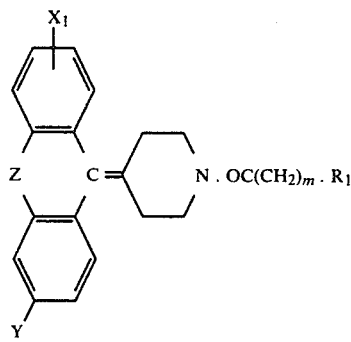

wherein $X_1$, Y, Z, m and $R_1$ are defined as follows:
$X_1$ is a halogen atom, an alkyl group with one to four carbon atoms inclusive, an alkoxy group with one to four carbon atoms inclusive, a methylmercapto group, or a trifluoromethyl group;
Y is hydrogen, fluorine, or a methyl group;
Z is oxygen or sulphur;
m is zero or an integer from one to two, inclusive; and
$R_1$ is a cycloalkyl group with four to six carbon atoms inclusive in the ring, which is substituted with one to four substituents selected from the group consisting of: amino; acetamino; mesylamino; and protected hydroxy- or protected hydroxymethyl, any such protected hydroxy or hydroxymethyl group present being protected by esterification into an ester of an aliphatic carboxylic acid having ten to twenty-two carbon atoms inclusive; and, when a previously-named substituent is present, also methyl.

2. A compound of the formula:

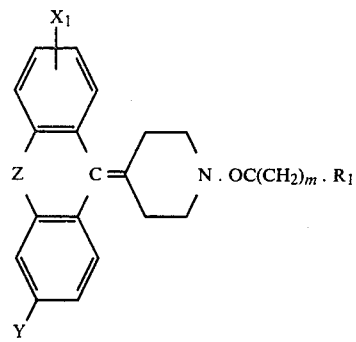

wherein $X_1$, Y, Z, m and $R_1$ are defined as follows:
$X_1$ is a halogen atom, an alkyl group with one to four carbon atoms inclusive, an alkoxy group with one to four carbon atoms inclusive, a methylmercapto group, or a trifluoromethyl group;
Y is hydrogen, fluorine, or a methyl group;
Z is oxygen or sulphur;
m is zero or an integer from one to two, inclusive; and
$R_1$ is a cycloalkyl group with four to six carbon atoms inclusive in the ring, which is substituted with one to four substituents selected from the group consisting of: amino; acetamino; and mesylamino; protected hydroxy- or protected hydroxymethyl and, when a previously-named substituent is present, also methyl; a five- or six-membered saturated heterocyclic ring having one or two hetero-atoms selected from oxygen and nitrogen atoms and being optionally substituted with a protected hydroxy group; any such protected hydroxy or hydroxymethyl group present being protected by esterification into an ester of an aliphatic carboxylic acid having ten to twenty-two carbon atoms inclusive.

3. A compound of claim 1 which is 1-(Trans-4-acetoxycyclohexanecarbonyl)-4-(2-trifluoromethyl-6-fluoro-9-thioxanthenylidene)piperidine.

* * * * *

UNITED STATES PATENT AND TRADEMARK OFFICE
CERTIFICATE OF CORRECTION

PATENT NO. : 4,275,209
DATED : June 23, 1981
INVENTOR(S) : Niels Lassen, Klaus P. Bøgesø, Peter B. Hansen, Jørn L. M. Buus and Allan J. Bigler It is certified that error appears in the above—identified patent and that said Letters Patent is hereby corrected as shown below:

[57] ABSTRACT, lines 10 & 11; "corresponds" should read -- correspond --
Col. 9, line 68; "Centrigrade" should read -- Centigrade --
Col. 14, line 45; "cid" should read -- acid --
Col. 19, line 1; "2-Methylthio-6-fluoro-9-thioxanthone" is a heading and should be centered.
Col. 19, line 44; "grams" should read -- gram --
Col. 21, line 4; "There" should read -- Where --
Col. 22, line 11; "results" should read -- result --
Col. 29, line 11; delete "the"

UNITED STATES PATENT AND TRADEMARK OFFICE
CERTIFICATE OF CORRECTION

PATENT NO. : 4,275,209

DATED : June 23, 1981

INVENTOR(S) : Niels Lassen, Klaus P. Bøgesø, Peter B. Hansen, Jørn L. M. Buus and Allan J. Bigler It is certified that error appears in the above—identified patent and that said Letters Patent is hereby corrected as shown below:

Col. 6, line 66; "1,2-cyclohexanedicaboxylic" should read
— 1,2-cyclohexanedicarboxylic —
Col. 10, line 56; "(Method b))" should read — (Method (b)) —
Col. 15, line 12; "-fluoro9-" should read — fluoro-9- —
Col. 17, lines 6 & 7; "drystallization" should read — crystallization —
Col. 27, line 50; "horses sheeps" should read — horses, sheep —
Col. 30, lines 39 & 40; "consising" should read — consisting —

Signed and Sealed this

First Day of December 1981

[SEAL]

Attest:

GERALD J. MOSSINGHOFF

Attesting Officer

Commissioner of Patents and Trademarks